(12) United States Patent
Kaltschmidt

(10) Patent No.: US 6,804,326 B2
(45) Date of Patent: Oct. 12, 2004

(54) X-RAY DIAGNOSTIC INSTALLATION AND HIGH-RESOLUTION DATA STORAGE METHOD THEREFOR

(75) Inventor: Rainer Kaltschmidt, Neunkirchen am Brand (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 10/602,895

(22) Filed: Jun. 24, 2003

(65) Prior Publication Data

US 2004/0005037 A1 Jan. 8, 2004

(30) Foreign Application Priority Data

Jul. 4, 2002 (DE) .......................................... 102 30 092

(51) Int. Cl.$^7$ ................................................. H05G 1/64
(52) U.S. Cl. ............................................. 378/98; 378/62
(58) Field of Search .......................... 378/62, 98, 98.2, 378/98.3, 106

(56) References Cited

U.S. PATENT DOCUMENTS 4,694,479 A * 9/1987 Bacskai et al. ............... 378/58
6,097,788 A * 8/2000 Berenstein et al. ........... 378/92

* cited by examiner

*Primary Examiner*—David V Bruce
(74) *Attorney, Agent, or Firm*—Schiff Hardin LLP

(57) ABSTRACT

In a method and an X-ray diagnostic installation for storing X-ray images, during a pulsed transillumination, new image datasets are produced averaging a number of temporally successive X-ray image datasets and the new image datasets are stored.

6 Claims, 5 Drawing Sheets

FIG 2
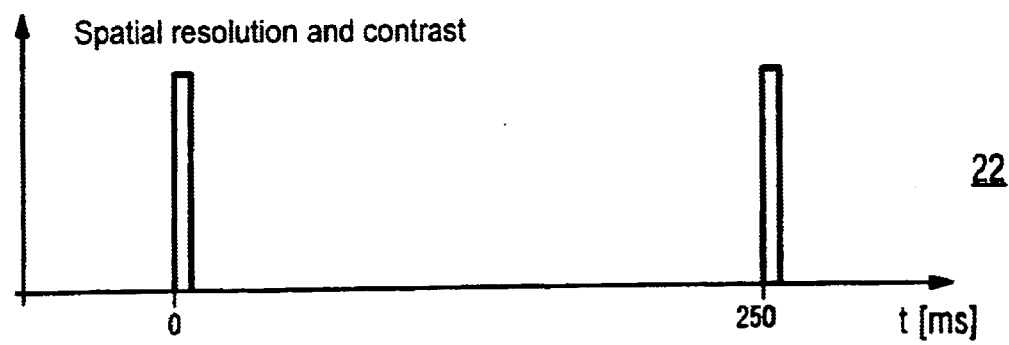
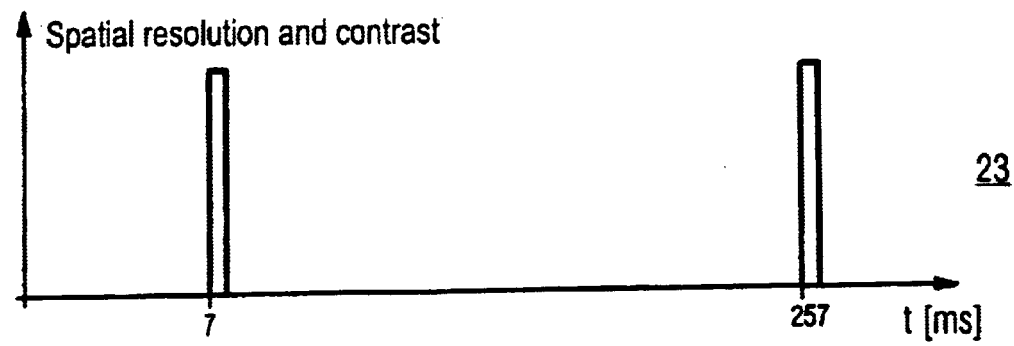

FIG 3
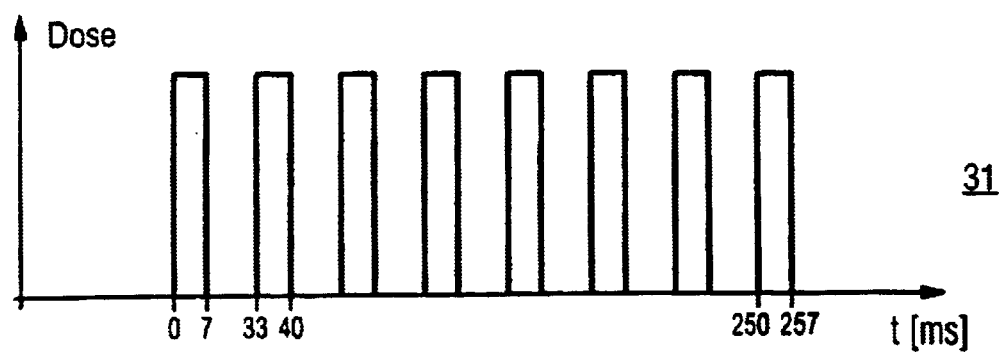
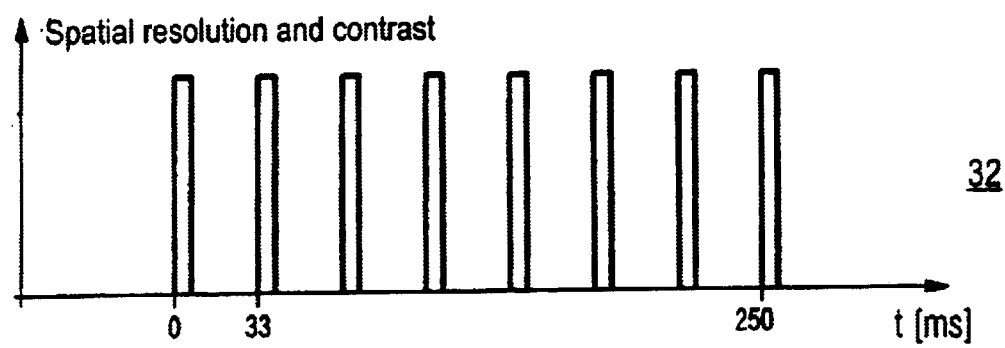
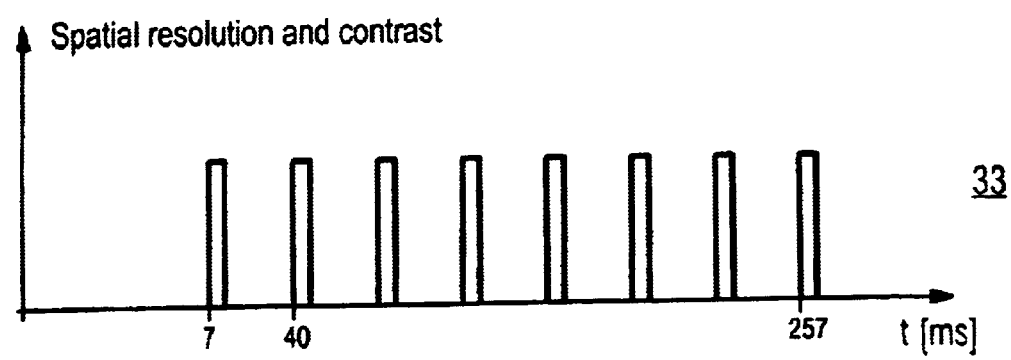

FIG 5
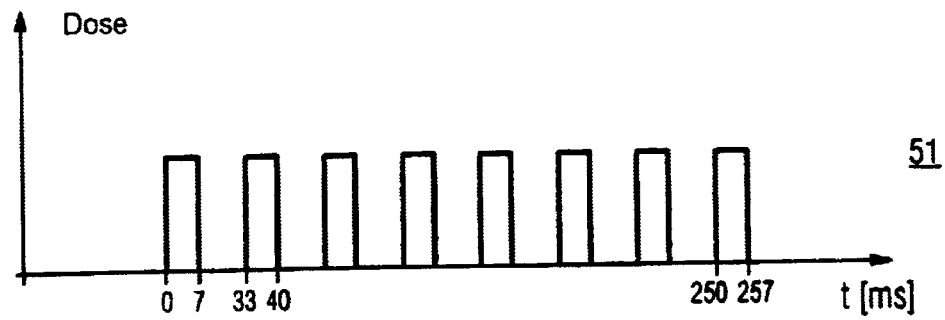
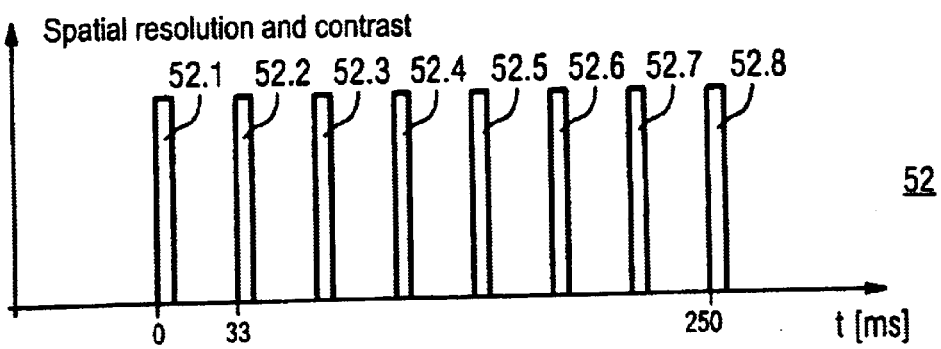
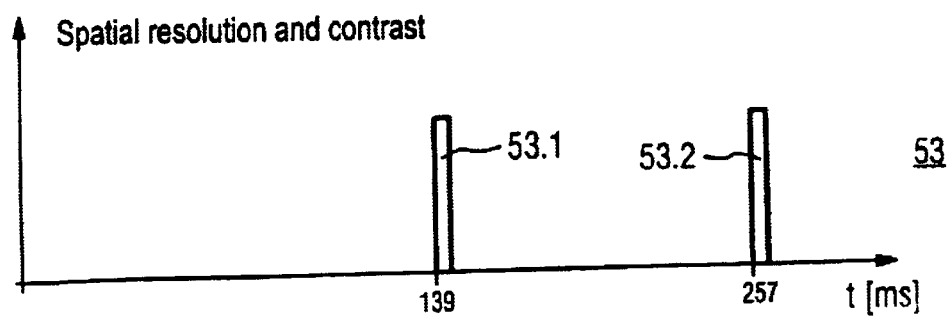

X-RAY DIAGNOSTIC INSTALLATION AND HIGH-RESOLUTION DATA STORAGE METHOD THEREFOR

BACKGROUND OF THE INVENTION

1. Field of the Invention

The present invention is directed to a method for storing X-ray image data and to an X-ray diagnostic installation operating according to the method.

2. Description of the Prior Art

During a pulsed transillumination of a patient, a series of temporally successive X-ray images of the patient is produced with an X-ray device, the series is displayed on a monitor, and the X-ray image data of to the series of X-ray images is stored. With an X-ray device employed for fluoroscopy, having an X-ray image intensifier, then the output signal of the X-ray image intensifier is converted into electrical signals, for example with semiconductor image sensors, so an X-ray image dataset arises for each X-ray image.

The X-ray images should exhibit an optimally high image quality. The image quality is determined by—among other things—the spatial resolution (digital aperture) of the X-ray image datasets allocated to the X-ray images and by an optimally high quantization of the individual picture elements (pixels). An optimally high spatial resolution corresponds to the demand for an image system with optimally many picture elements and logically leads to the introduction of high-resolution video cameras, so that the X-ray images can be digitized with, for example, up to 1024×1024 pixels. By contrast, the quantization of the individual picture elements influences the contrast resolution of the X-ray images. In particular, the spatial resolution and quantization can be improved by means of additional hardware outlay, however, the size of the corresponding X-ray image datasets also increases with increasing resolution.

The image quality also can be degraded by a movement on the part of the patient produced, for example, by respiration or heartbeat. This effect is mathematically acquired by expanding the resolution term in the time dimension and is particularly dependent on the exposure time for the individual X-ray images. In the fluoroscopy mode, for example, each X-ray image of the series of X-ray images is exposed for approximately 30 ms, and approximately 30 X-ray images per second are produced. An image frequency of 50 X-ray images per second is even realized in some applications. Given short exposure times of approximately 7 ms per X-ray image, moreover, the relevant legal restrictions allow an increased dose compared to the fluoroscopy mode, so the signal-to-noise ratio of the X-ray image can be increased.

As already mentioned, the X-ray image data are stored, for example, on a hard disk. The speed with which the data can be stored on a hard disk is particularly defined by its write-read rate. A data rate of the supplying PCI bus in the peripheral equipment can also negatively influence the data rate with which the data are written onto the hard disk. It is therefore generally not possible to store a series of high-resolution X-ray image datasets that were produced with a high image frequency on a hard disk.

The size of the X-ray image datasets can be reduced for storage by, for example, the quantization of the picture elements or the spatial resolution of the corresponding X-ray images being reduced. This, however, leads to a degradation of the image quality. Another possibility is to reduce the image frequency in the acquisition of the X-ray images. In the case of dynamic events, however, this can lead to a buckling of the exposure, known as the Mickey Mouse effect. Another possibility is to employ a multiple hard disk system with suitable controller electronics. Multiple hard disk system is relatively expensive compared to a single hard disk.

SUMMARY OF THE INVENTION

It is an object of the invention to provide a method that enables storage of high-resolution X-ray image data during a transillumination. A further object of the invention is to provide an X-ray diagnostic installation wherein storage of X-ray image data produced during the transillumination can be flexibly manipulated.

The first object of the invention is achieved in a method for storing X-ray image data that includes the steps of: producing a series of X-ray image datasets of an examination subject during a pulsed transillumination, producing a first image dataset by averaging of a number of the temporally successive X-ray image datasets, storing the first image dataset, producing a second image dataset by averaging further temporally successive X-ray image datasets that immediately temporally follow the X-ray image datasets allocated to the first image dataset, and storing the second image dataset.

The series of X-ray image datasets of the examination subject, for example a patient, is produced in the context of the transillumination. When the X-ray device employed for the transillumination has an X-ray image intensifier, the output signal of the X-ray image intensifier is digitized, as already mentioned. As a result an X-ray image dataset arises for each X-ray image. If the X-ray device is equipped with a flat image detector, then the series of X-ray image datasets is produced by a well known readout of the detector elements of the flat image detector and subsequent processing of the signals that have been read out. The X-ray images allocated to the individual X-ray image datasets are observed with a viewing device during the transillumination.

Inventively, the image datasets are subsequently produced from a number of temporally successive X-ray image datasets by averaging. In a to preferred embodiment of the invention, the averages are formed by integration of the corresponding picture elements of the respective X-ray image datasets or by a sliding, weighted averaging. The image datasets are subsequently stored. Preferably the image datasets are stored on a hard disk.

Before the storage, consequently, a number of temporally successive X-ray image datasets are combined into one image dataset, resulting in a series of image datasets arising whose image frequency is lower than the image frequency of the series of X-ray image datasets. The lower image frequency results in a lower data rate, for which reason the series of image datasets can be, in particular, transmitted onto a hard disk. Due to the reduced image frequency, the image datasets can have the same spatial resolution and quantization as the X-ray image datasets, so the resolution of the corresponding images corresponds to that of the X-ray images allocated to the X-ray image datasets. As a result of the averaging, moreover, the signal-to-noise ratio of the images allocated to the image datasets can be increased compared to the X-ray images allocated to the X-ray image datasets. This effect can be utilized in order to reduce the X-ray dose during the transillumination. If a CCD camera is employed for the transillumination, in particular, the iris of the CCD camera can be opened further. This corresponds to a lower depth of field and a greater tolerance to contamination of the output window of the X-ray image intensifier. Further, the CCD chip can be driven better, which in turn has a positive effect on the signal-to-noise ratio.

The second object of the invention is achieved in an X-ray diagnostic installation for the implementation of pulsed transillumination of a subject wherein the X-ray image data are stored according to the inventive method.

The X-ray diagnostic installation can have a selection unit with which a method for storing X-ray image data is selectable, from a set of methods for storing X-ray image data, before the transillumination. One of the methods for storing X-ray image data proceeds according to the above-described, inventive method. A method for storing X-ray image data, for example based on data compression of the X-ray image sets as described in the introduction, may be another selectable method.

An advantage of the inventive X-ray diagnostics installation is that a physician implementing the transillumination can determine the storage strategy by deciding decides whether a high temporal resolution or a high static image quality is preferred. A combination of the reduction of the contrast resolution, the spatial resolution or the temporal resolution is also possible.

DESCRIPTION OF THE DRAWINGS

FIGS. 2 and 3 show graphics for illustrating methods for storing X-ray image data.

FIGS. 4 and 5 show graphics for illustrating the inventive method.

DESCRIPTION OF THE PREFERRED EMBODIMENTS

Figure 1:
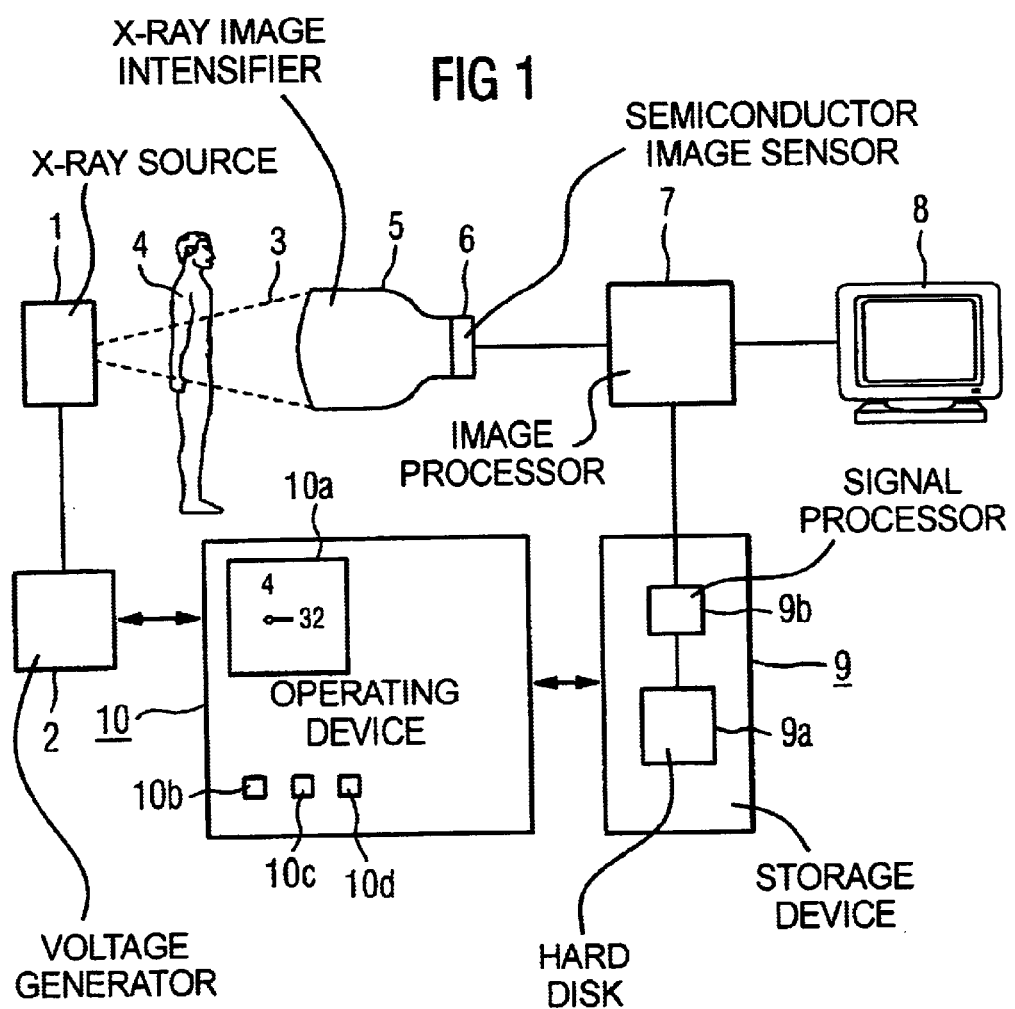
FIG. 1 is a schematic block diagram of an inventive X-ray diagnostics installation.

The X-ray diagnostic installation shown partly as a block diagram in FIG. 1 is provided for the implementation of a pulsed transillumination of a patient 4. It has an X-ray source 1 that is operated by a voltage generator 2. The X-ray source 1 emits pulsed X-ray bundles 3, having a duration of 7 ms in the exemplary embodiment, that penetrate the patient 4 and are incident on an X-ray image intensifier 5 as X-ray images attenuated dependent on the transparency of the patient 4. Whether the X-ray source 1 emits four or thirty-two X-ray bundles 3 per second during a transillumination can be set with a switch 10a of an operating device 10 in the exemplary embodiment. Dependent on this setting, consequently, four or thirty-two X-ray images per second are incident on the X-ray image intensifier 5. The operating device in the exemplary embodiment also has keys 10b through 10e, the functions of which are described below.

The X-ray image intensifier 5 is followed by a semiconductor image sensor 6 with suitable electronics that converts the output signal of the X-ray image intensifier 5 into electrical signals, so that an X-ray image dataset arises from each X-ray image incident on the X-ray image intensifier 5. In the exemplary embodiment, the X-ray image datasets are quantized with 12 bits and have a spatial resolution of 1024×1024 picture elements.

The electrical signals, i.e. the X-ray image datasets, are supplied to a digital image processing device 7 that processes the image datasets in a way known to those skilled in the art, so that X-ray images allocated to the X-ray image datasets are displayed at a monitor 8 connected to the image processing device 7.

In the exemplary embodiment, the image processing device 7 also is connected to a storage device 9 that is essentially formed by a hard disk 9a with a preceding signal processing device 9b. Dependent on a setting with the operating device 10 determined before the transillumination, the signal processing device 9b processes the X-ray image datasets produced during the transillumination into image datasets. Dependent on the setting, the X-ray image datasets or the image datasets are stored on the hard disk 9a. The individual operating modes are set with the keys 10b through 10e and the switch 10a of the operating device 10 before the transillumination.

In a first operating mode, which is shown in FIG. 2 and is set by a corresponding position of the switch 10a in the exemplary embodiment, the X-ray diagnostic installation is operated such that the X-ray source 1 emits four X-ray bundles 3 per second having a duration of 7 ms (graphic 21), so that four X-ray image datasets with 12-bit quantization and 1024×1024 picture elements are communicated to the image processing device 7. Each of the X-ray image datasets is immediately communicated to the signal processing device 9b (graphic 22), which forwards them to the hard disk 9a (graphic 23). The X-ray image datasets are subsequently stored on the hard disk 9a.

In a second operating mode, which is shown in FIG. 3 and is set by a corresponding position of the switch 10a and by pressing the key 10b in the exemplary embodiment, the X-ray diagnostics installation is operated such that the X-ray source 1 emits thirty-two X-ray bundles 3 with a 7 ms duration per second (graphic 31), so that thirty-two X-ray image datasets with 12-bit quantization and 1024×1024 picture elements are communicated to the image processing device 7. Each of the X-ray image datasets is immediately communicated to the signal processing device 9b (graphic 32). In response thereto, the signal processing device 9b produces a further image dataset from each incoming X-ray image dataset by subjecting the incoming X-ray image dataset to a data reduction according to well known methods, such that the arising image dataset exhibits a lower quantization and spatial resolution. In the present exemplary embodiment, the data-reduced image datasets exhibit a spatial resolution of 512×512 picture elements and a quantization of 8 bits. After the production of a data-reduced image dataset, the signal processing device 9b communicates the data-reduced image dataset to the hard disk 9a in which the data-reduced image datasets are stored (graphic 33).

Figure 4:
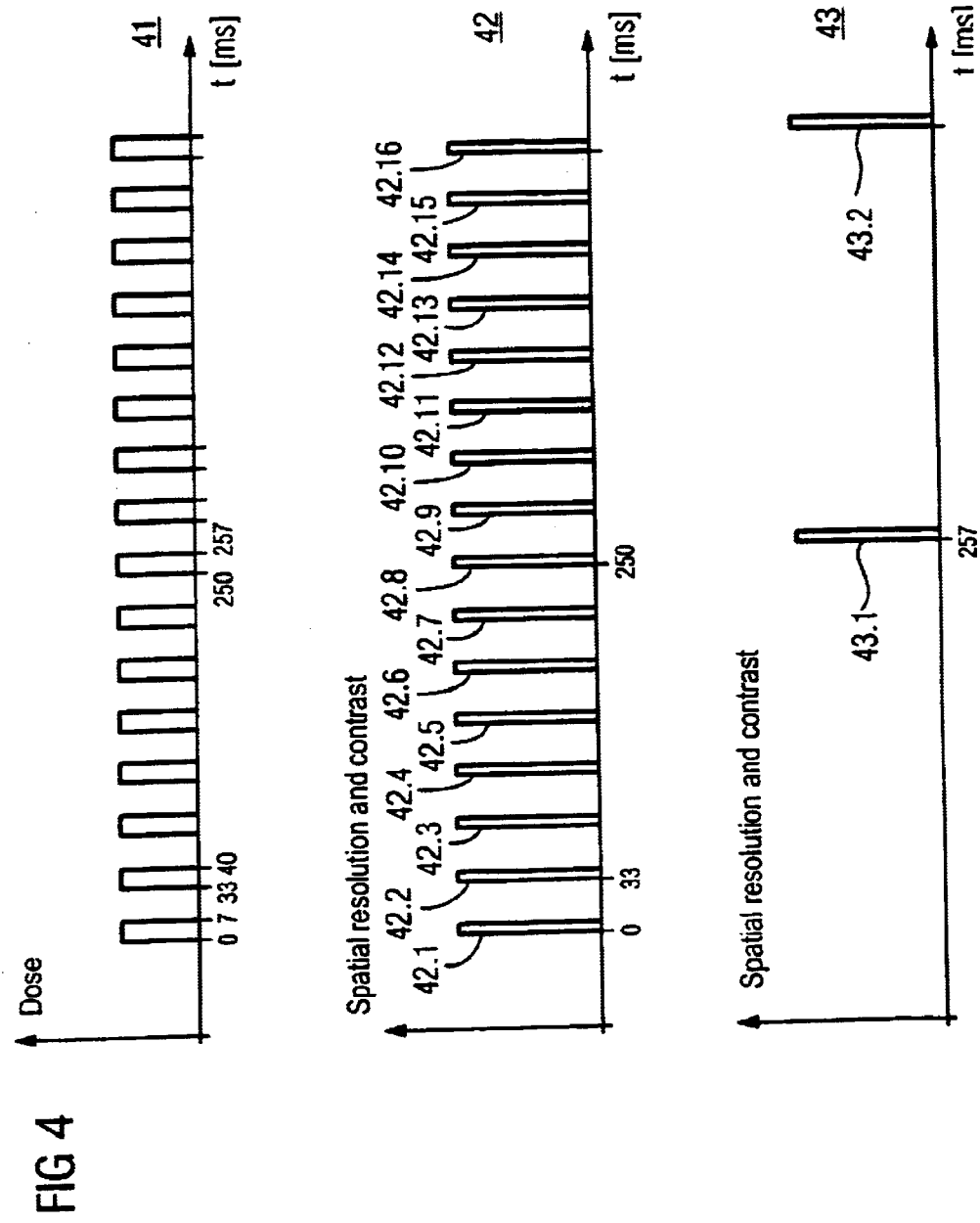

In a third operating mode, which is illustrated in FIG. 4 and is set by a corresponding position of the switch 10a and by pressing the key 10c in the exemplary embodiment, the X-ray diagnostics installation is again operated such that the X-ray source 1 emits thirty-two X-ray bundles 3 with a duration of 7 ms per second (graphic 41), so that thirty-two X-ray image datasets with 12-bit quantization and 1024× 1024 picture elements are communicated to the image processing device 7. Each of the X-ray image datasets is immediately communicated to the signal processing device 9b (graphic 42). This numerically adds the values of the individual picture elements of eight (in the exemplary embodiment) temporally successive X-ray image datasets 42.1 through 42.8, with a new image dataset 43.1 arising therefrom. The image dataset 43.1 arising due to the integration of the X-ray image datasets 42.1 through 42.8 likewise contains 1024×1024 picture elements with 12-bit quantization and is forwarded to the hard disk 9a for storage (graphic 43). Subsequently, the signal processing device 9b integrates the picture elements of another eight temporally successive X-ray image datasets 42.9 through 42.16 to produce a further image dataset 43.2 and communicates said further image dataset 43.2 to the hard disk 9a for storage. Due to the integration of the X-ray image datasets 42.1 through 42.8 or 42.9 through 42.16, the signal-to-noise ratios of the respective image datasets 43.1 and 43.2 are increased compared to the signal-to-noise ratios of the X-ray image datasets 42.1 through 42.8 or 42.9 through 42.16. A lower X-ray dose therefore can be applied than in the first and second operating modes.

In a fourth operating mode, which is illustrated in FIG. 5 and is set by a corresponding position of the switch 10a and by pressing the key 10d in the exemplary embodiment, the X-ray diagnostic installation is again operated such that the X-ray source 1 emits thirty-two X-ray bundles 3 with a duration of 7 ms per second (graphic 51), so that thirty-two X-ray image datasets with 12-bit quantization and 1024× 1024 picture elements are communicated to the image processing device 7. Each of the X-ray image datasets is immediately communicated to the signal processing device 9b (graphic 52). The signal processing device 9b numerically adds the values of the individual picture elements of four (in the present exemplary embodiment) temporally successive X-ray image datasets 52.1 through 52.4 and subjects the image dataset 53.1 resulting therefrom to a data reduction, to a resolution of 1024×512 picture elements with a quantization of 12 bits. The image dataset 53.1 arising from the integration and subsequent data reduction of the X-ray image datasets 52.1 through 52.4 is subsequently forwarded to the hard disk 9a for storage (graphic 43). Subsequently, the signal processing device 9b integrates the picture elements of another four temporally successive X-ray image datasets 52.5 through 52.8 to produce a further image dataset 53.2, reduces the spatial resolution to 1024× 512 picture elements, and communicates the further image dataset 53.2 to the hard disk 9a for storage.

The image datasets 43.1, 43.2, 53.1 and 53.2 also can be produced from the X-ray image datasets 42.1 through 42.8, 42.9 through 42.16, 52.1 through 52.4 or 52.5 through 52.8 by means of other methods. In particular, a sliding, weighted averaging is possible. The image frequencies and the X-ray pulse duration of 7 ms are only examples.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for storing X-ray image data comprising the steps of:

producing a series of temporally successive image datasets by pulsed transillumination of an examination subject;

producing a first image dataset by averaging a first plurality of said temporally successive X-ray image datasets;

storing said first image dataset;

producing a second image dataset by averaging a second plurality of said temporally successive X-ray image datasets immediately following said first plurality and allocated to said first image dataset; and storing said second image dataset.

2. A method as claimed in claim 1 comprising averaging each of said first and second pluralities of said temporally successive X-ray image datasets by a sliding, weighted averaging.

3. A method as claimed in claim 1 comprising storing each of said first and second image datasets on a hard disk.

4. An X-ray diagnostic installation comprising:

an X-ray image generating apparatus adapted to interact with an examination subject, said X-ray image generating apparatus emitting X-rays in a pulsed transillumination of the subject to produce a series of temporally successive X-ray image datasets;

an image processor supplied with said series for producing a first image dataset by averaging a first plurality of said temporally successive X-ray image datasets, and for producing a second image dataset by averaging a second plurality of said temporally successive X-ray image datasets following said first plurality and allocated to said second image dataset; and a storage arrangement connected to said image processor in which said first image dataset and said second image dataset are stored.

5. An X-ray diagnostic installation as claimed in claim 4 wherein said image processor produces said first image dataset by a sliding, weighted averaging of said first plurality of said temporally successive X-ray image datasets, and produces said second image dataset by a sliding, weighted averaging of said second plurality of said temporally successive X-ray image datasets.

6. An X-ray diagnostic installation as claimed in claim 4 wherein said storage arrangement comprises a hard disk on which said first image dataset and said second image dataset are stored.

* * * * *